US012746373B2

(12) United States Patent
Singla

(10) Patent No.: US 12,746,373 B2
(45) Date of Patent: Sep. 29, 2026

(54) GUIDE CATHETER AND METHODS OF USING THE SAME

(71) Applicant: RUTGERS, THE STATE UNIVERSITY OF NEW JERSEY, New Brunswick, NJ (US)

(72) Inventor: Amit Singla, New Brunswick, NJ (US)

(73) Assignee: RUTGERS, THE STATE UNIVERSITY OF NEW JERSEY, New Brunswick, NJ (US)

(*) Notice: Subject to any disclaimer, the term of this patent is extended or adjusted under 35 U.S.C. 154(b) by 50 days.

(21) Appl. No.: 18/993,296

(22) PCT Filed: Aug. 8, 2023

(86) PCT No.: PCT/US2023/029735

§ 371 (c)(1),
(2) Date: Jan. 10, 2025

(87) PCT Pub. No.: WO2024/035705

PCT Pub. Date: Feb. 15, 2024

(65) Prior Publication Data

US 2026/0115430 A1 Apr. 30, 2026

Related U.S. Application Data

(60) Provisional application No. 63/396,315, filed on Aug. 9, 2022.

(51) Int. Cl.
*A61M 25/10* (2013.01)
*A61M 25/00* (2006.01)

(52) U.S. Cl.
CPC ........ *A61M 25/10* (2013.01); *A61M 25/0045* (2013.01); *A61M 25/0053* (2013.01);
(Continued)

(58) Field of Classification Search
CPC .............. A61M 25/10; A61M 25/0045; A61M 25/0053; A61M 2025/1052; A61M 2025/1079; A61M 2205/0238
See application file for complete search history.

(56) References Cited

U.S. PATENT DOCUMENTS 5,855,546 A 1/1999 Hastings et al.
6,099,454 A 8/2000 Hastings et al.
(Continued)

FOREIGN PATENT DOCUMENTS

CN 105311730 A 2/2016
CN 106691533 A 5/2017
(Continued)

OTHER PUBLICATIONS

Baek, et al., "Balloon Guide Catheter Is Beneficial in Endovascular Treatment Regardless of Mechanical Recanalization Modality", Stroke 50, 1490-1496, DOI: 10.1161/STROKEAHA.118.024723 (2019).

(Continued)

*Primary Examiner* — Vi X Nguyen
(74) *Attorney, Agent, or Firm* — VIKSNINS HARRIS PADYS MALEN LLP

(57) ABSTRACT

Described herein is a guide catheter, including: a catheter tube having a catheter lumen, a first opening, and a second opening; and a balloon surrounding the catheter tube. In the guide catheter, the length of the section of the catheter tube between the balloon and the second opening ranges from about 8 cm to about 25 cm. Also described herein are methods of using the guide catheter.

16 Claims, 2 Drawing Sheets

(52) U.S. Cl.
CPC ............... *A61M 2025/1052* (2013.01); *A61M 2025/1079* (2013.01); *A61M 2205/0238* (2013.01)

(56) References Cited

U.S. PATENT DOCUMENTS

| | | | | |
|---|---|---|---|---|
| 8,021,351 | B2 | 9/2011 | Boldenow et al. | |
| 8,206,370 | B2 | 6/2012 | Von et al. | |
| 8,252,015 | B2 | 8/2012 | Leeflang et al. | |
| 8,926,560 | B2 | 1/2015 | Dinh et al. | |
| 9,408,955 | B2 * | 8/2016 | Jenkins | A61B 17/12104 |
| 10,456,519 | B2 * | 10/2019 | Ngo-Chu | A61M 1/77 |
| 2006/0189921 | A1 | 8/2006 | Galdonik et al. | |
| 2007/0060911 | A1 | 3/2007 | Webster et al. | |
| 2007/0293846 | A1 | 12/2007 | Von et al. | |
| 2009/0076447 | A1 | 3/2009 | Casas et al. | |
| 2012/0071838 | A1 | 3/2012 | Fojtik | |
| 2013/0253417 | A1 | 9/2013 | Dinh et al. | |
| 2014/0243873 | A1 | 8/2014 | Franklin | |
| 2015/0112307 | A1 | 4/2015 | Margolis | |
| 2016/0250397 | A1 | 9/2016 | Griffin et al. | |
| 2021/0169509 | A1 | 6/2021 | Goyal | |
| 2021/0252260 | A1 | 8/2021 | Maini | |
| 2021/0361910 | A1 | 11/2021 | Mullins et al. | |

FOREIGN PATENT DOCUMENTS

| | | | |
|---|---|---|---|
| CN | 110339461 | A | 10/2019 |
| CN | 111110310 | A | 5/2020 |
| CN | 211357363 | U | 8/2020 |
| WO | 2018208622 | A1 | 11/2018 |

OTHER PUBLICATIONS

Cortez, et al., "Navigating the Walrus: a Large Bore Balloon Guide Catheter for Acute Ischemic Stroke Thrombectomy", P-013, J NeuroIntervent Surg, 13 (Suppl 1), 10.1136/neurintsurg-2021-SNIS.49, 1 page (2021).
Dossani, et al., "Use of a sheathless 8-French balloon guide catheter (Walrus) through the radial artery for mechanical thrombectomy: technique and case series", J NeuroIntervent Surg 14, 517-520 (2022).
Goyal, et al., "Balloon guide catheters: use, reject, or randomize?", Neuroradiology 63, 1179-1183 (2021).
Liu, et al., "Safety and efficacy of the SeparGate™ balloon-guiding catheter in neurointerventional surgery: Study protocol of a prospective multicenter single-arm clinical trial", Journal of Interventional Medicine 3, 93-97 (2020).
Patent Cooperation Treaty, International Search Report and Written Opinion for PCT/US2023/029735, 9 pages dated Jan. 29, 2024.

* cited by examiner

GUIDE CATHETER AND METHODS OF USING THE SAME

RELATED APPLICATIONS

This application claims priority to U.S. Provisional Application No. 63/396,315 that was filed on Aug. 9, 2022. The entire content of the application referenced is hereby incorporated by reference herein.

BACKGROUND

Guide catheters provide support for device advancement during the removal of thrombus as part of treatment and/or prevention of, for example, stroke, heart attack, and/or necrosis in the body. Guide catheters are moved to a site in vasculature near the treatment site so that procedural devices such as aspiration catheters or stent-retrievers can be advanced through the guide catheter to the treatment site to remove the thrombus.

Guide catheters with a balloon called balloon guide catheters (BGCs), are used for stroke interventions to prevent distal embolization: in that case, the thrombus is retrieved by, for example, an aspiration catheter by creating a proximal flow arrest. Current BGCs have a balloon located near the distal end of the catheter typically within 1-2 cm of the distal end. Researchers have suggested that balloon guide catheters decrease distal embolization rates and improve recanalization rates and functional outcomes as compared to the conventional guide catheters.

However, an addition of a balloon adds to the stiffness of the catheters and navigating BGCs to desirable sites to provide adequate support to the interventional catheters for the treatment of strokes can be challenging. Current BGCs have limited hydrophilic coating due to the distal balloon which limits the navigability. Furthermore, the current BGCs induce vasospasm of the blood vessel due to stiffness and friction between the catheter and the vessel wall. Accordingly, there is a need for novel balloon guide catheters that can be navigated with relative ease to the desired location. The present invention addresses this need.

BRIEF DESCRIPTION OF THE DRAWINGS

The following detailed description of exemplary embodiments will be better understood when read in conjunction with the appended drawings. For the purpose of illustrating, non-limiting embodiments are shown in the drawings. It should be understood, however, that the instant specification is not limited to the precise arrangements and instrumentalities of the embodiments shown in the drawings.

DETAILED DESCRIPTION

Figure 1A:
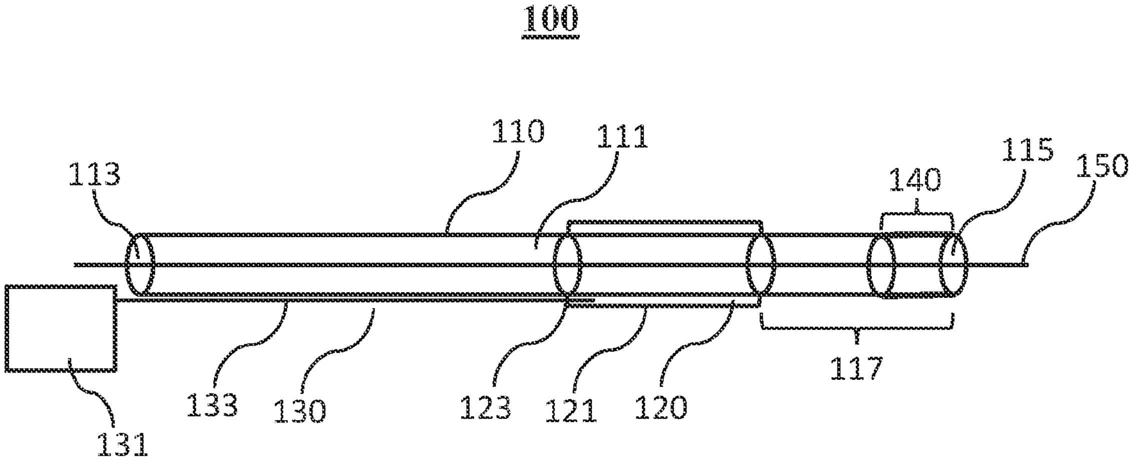
FIGS. 1A-1B are side view illustrations of a balloon guide catheter in accordance with some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

The present study addresses certain issues causing the undesirable navigability in the conventional balloon guide catheters. In conventional BGCs, the balloon is located approximately 1 cm to 2 cm proximal to the distal end of the catheters. In certain embodiments, balloons near the distal end of the balloon guide catheters limit the flexibility of the distal portion of the catheter and, as a result, limit the navigability. Furthermore, the balloons near the distal end of the catheter, limit the hydrophilic coating of the catheters on that distal portion. The limited flexibility and the limited hydrophilic coating increase the friction between the catheter and the vessel wall, causing vasospasm which can delay the procedure or limit the procedure.

The present study further discovered that the above issues can be resolved if the balloon is placed further away from the distal end, such as between 10 cm to 20 cm proximal to the distal end of the guide catheter. When the balloon is located more proximal on the catheter, the distal part of the catheter be made sufficiently flexible and can be navigated comparatively easily, such as into the distal common carotid artery or internal carotid artery. Having a more proximal balloon also enables the extension of the hydrophilic coating to the distal end of the catheter, reducing friction and resulting in easier access into the vascular lumen.

Accordingly, in some aspects, the present invention is directed to a balloon guide catheter.

In some aspects, the present invention is directed to a method of navigating a balloon guide catheter.

DEFINITIONS

As used herein, each of the following terms has the meaning associated with it in this section. Unless defined otherwise, all technical and scientific terms used herein generally have the same meaning as commonly understood by one of ordinary skill in the art to which this disclosure belongs. Generally, the nomenclature used herein and the laboratory procedures in animal pharmacology, pharmaceutical science, peptide chemistry, and organic chemistry are those well-known and commonly employed in the art. It should be understood that the order of steps or order for performing certain actions is immaterial, so long as the present teachings remain operable. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the application, where an element or component is said to be included in and/or selected from a list of recited elements or components, it should be understood that the element or component can be any one of the recited elements or components and can be selected from a group consisting of two or more of the recited elements or components.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B."

"About" as used herein when referring to a measurable value such as an amount, a temporal duration, and the like, is meant to encompass variations of ±20% or ±10%, in certain embodiments ±5%, in certain embodiments ±1%, in certain embodiments ±0.1% from the specified value, as such variations are appropriate to perform the disclosed methods.

Guide Catheter

In some aspects, the present invention is directed to a guide catheter. In some embodiments, the guide catheter is a balloon guide catheter.

Figure 1B:
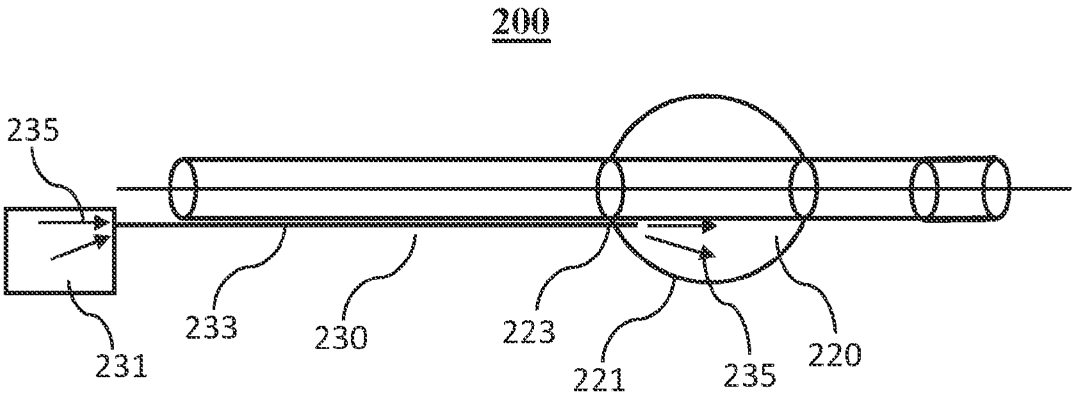

FIGS. 1A-1B describe a non-limiting embodiment of the catheter. It is worth noting that individual elements shown in FIGS. 1A-1B do not have to be combined with other elements of the same figure. One of ordinary skill in the art would understand that these elements can be combined with other elements shown in the other figure, or elements not shown in the figures.

Referring to FIG. 1A, in some embodiments, the guide catheter 100 includes a catheter tube 110 having a catheter lumen 111, a first opening 113 for remaining outside the body of a patient during treatment and a second opening 115 for inserting into the body of the patient.

In some embodiments, the length of the catheter tube 110 ranges from about 80 cm to about 110 cm, such as from about 90 cm to about 110 cm, from about 80 cm to about 105 cm, from about 85 cm to about 100 cm, or from about 90 cm to about 95 cm. In some embodiments, the length of the catheter tube 110 is about 80 cm, about 85 cm, about 90 cm, about 95 cm, about 100 cm, about 105 cm, about 110 cm, about 115 cm, about 120 cm, or any ranges there between.

In some embodiments, the outer diameter of the catheter tube 110 ranges from about 2 mm to about 3.5 mm, such as from about 2.1 mm to about 3.5 mm. In some embodiments, the outer diameter of the catheter tube 110 is about 2.0 mm, about 2.1 mm, about 2.2 mm, about 2.3 mm, about 2.4 mm, about 2.5 mm, about 2.6 mm, about 2.7 mm, about 2.8 mm, about 2.9 mm, about 3.0 mm, about 3.1 mm, about 3.2 mm, about 3.3 mm, about 3.4 mm, about 3.5 mm or any ranges therebetween.

In some embodiments, the diameter of the catheter lumen 111 ranges from about 1.8 mm to about 2.5 mm, such as from about 2.1 mm to about 2.5 mm. In some embodiments, the diameter of the catheter lumen 111 is about 1.8 mm, 1.9 mm, 2.0 mm, about 2.1 mm, about 2.2 mm, about 2.3 mm, about 2.4 mm, about 2.5 mm, or any ranges therebetween.

In some embodiments, the guide catheter 100 further includes a balloon 120 surrounding the catheter tube 110. In some embodiments, the balloon 120 includes a flexible balloon material 121 having an opening/s 123 for the inflation of the balloon 120.

In some embodiments, the length of the balloon 120 surrounding the catheter tube 110 ranges from 5 mm to about 15 mm, such as from 6 mm to about 14 mm, from 7 mm to about 13 mm, from 8 mm to about 12 mm, or from 9 mm to about 11 mm. In some embodiments, the length of the balloon 120 surrounding the catheter tube 110 is about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, or any ranges therebetween.

In some embodiments, the flexible balloon material 121 is made from or includes a nylon material, a polyester material, a polyether block amide (PEBA) material, a polyurethane material, a silicone material, or the like. In some embodiments, the balloon 120 is a compliant balloon (i.e., balloon 120 conforms to the shape of the inner wall of blood vessels when inflated), and the flexible balloon material 121 is made from or includes a material suitable for compliant balloons, such as a polyurethane material, a silicone material, or the like.

In some embodiments, the section 117 of the catheter tube 111 between the balloon 120 and the second opening 115 of the catheter tube has a length ranging from about 8 cm to about 25 cm, such as from about 9 cm to about 22.5 cm, from about 10 cm to about 20 cm, from about 11 cm to about 17.5 cm, or about 12 cm to about 15 cm. In some embodiments, the section 117 has a length of about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, about 21 cm, about 22 cm, about 23 cm, about 24 cm, about 25 cm, or any ranges therebetween.

In some embodiments, the section 117 of the catheter tube 111 has a variable stiffness. In some embodiments, the stiffness of the catheter tube 111 in section 117 decreases gradually as approaching the second opening 115. In some embodiments, the stiffness of the catheter tube 111 in proximity to the balloon 120 is sufficiently high that the portion of the catheter tube 111 in proximity to the balloon 120 is not substantially bent at the origins of the great vessels. The present study discovered that, when the section 117 has the stiffness configuration as described in this paragraph, the catheter 100 conforms better to the vascular anatomy of the carotid and subclavian arteries origin from radial approach, and thus has desirable navigability for radial approach in neurointerventions (i.e., the endovascular treatment of vascular disorders of the brain, spinal cord, head and neck). In some embodiments, the stiffness of the catheter tube 111 in section 117 is gradually decreased as approaching the second opening 115 by decreasing the coil density in the side wall of the catheter tube 111, or by the elimination of braids in the side wall.

In some embodiments, the section 117 of the catheter tube 111, or a portion thereof in proximity to the second opening 115 has a hydrophilic coating on an outer surface thereof. In some embodiments, the hydrophilic coating reduces the friction between the catheter tube 110 and the inner wall of the blood vessel, making the navigation of the catheter 100 inside the blood vessel relatively easier. In some embodiments, the length of the portion of the catheter tube 111 from the second opening 115 that has the hydrophilic coating ranges from about 0 cm to about 25 cm, such as from about 5 cm to about 25 cm, from about 7.5 cm to about 22.5 cm, from about 10 cm to about 20 cm, or from about 12.5 cm to about 17.5 cm. In some embodiments, the length of the portion of the catheter tube 111 from the second opening 115 that has the hydrophilic coating is about 0 cm, about 1 cm, about 2 cm, about 3 cm, about 4 cm, about 5 cm about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, about 21 cm, about 22 cm, about 23 cm, about 24 cm, about 25 cm, or any ranges therebetween. In some embodiments, the length of the portion of the catheter tube 111 from the second opening 115 that has the hydrophilic coating is the same as described above, but not 0 cm. In some embodiments, the hydrophilic coating extends over the distal (i.e., closer to the second opening 115 of the catheter tube 110) 20-25 cm of the catheter, reaching to the distal end of the catheter. In some embodiments, the hydrophilic coating is a polysaccharide coating, a poly(acrylic acid) coating, or the like.

In some embodiments, the catheter 110 further includes an inflator 130 for inflating the balloon 120. In some embodiments, the inflator 130 includes a pump 131 for forcing a movement of a fluid (liquid such as contrast and saline mixture) and a tube 133 connecting the pump 131 and the balloon 120 such that the pump 131 and the interior of the balloon 120 are in fluid communication. In some embodiments, the tube 133 is inserted into the balloon 120 via the opening 123. In some embodiments, the pump 131 is a mechanical pump, a syringe, or the like.

Referring to FIG. 1B, when the balloon 220 is being inflated, the pump 231 forces a fluid 235 in to the balloon 220 via the tube 233 and the opening 223, causing the flexible balloon material 221 to expand. In some embodiments, the fluid is air, a gas such as nitrogen gas, or a liquid such as water, a contrast medium, a saline or mixtures thereof. In some embodiments, a cross-sectional diameter of the inflated balloon 220 ranges from about 5 mm to about 18 mm, such as from about 6 mm to about 17 mm, from about 7 mm to about 16 mm, from about 8 mm to about 15 mm, from about 9 mm to about 14 mm, from about 10 mm to about 13 mm. In some embodiments, the cross-sectional diameter of the inflated balloon 220 is about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, or any ranges therebetween.

It is worth noting that, although in FIGS. 1A and 1B the tube 133/233 runs outside the catheter tube 110/210 and the opening 123/223 is on the flexible balloon material 121/221, all alternative configurations of the balloons and inflators are within the scope of the present invention.

Figure 2A:
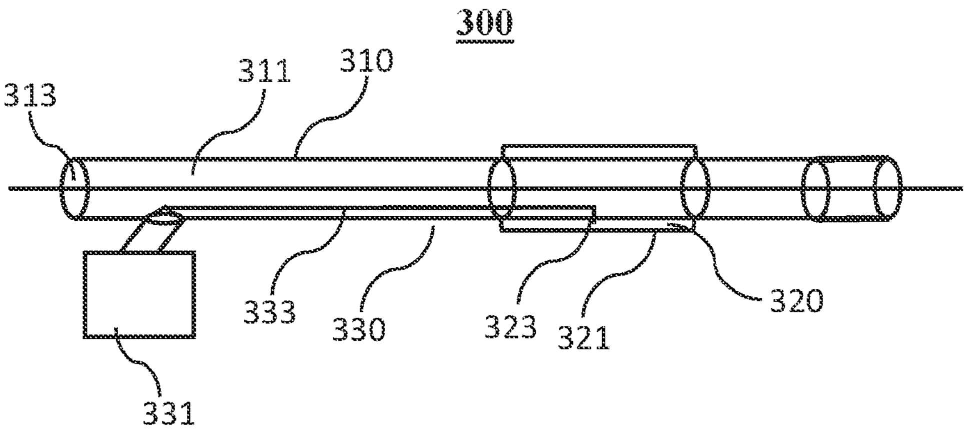
FIGS. 2A-2B are side view illustrations and or cross-sectional view illustrations of a balloon guide catheter in accordance with some embodiments.

For example, referring to FIG. 2A, in some embodiments, the tube 333 runs inside the catheter lumen 311 and the opening 323 is on an outer wall of the catheter tube 310 within the coverage of the balloon 320 and the opening 323 passes through the outer wall of the catheter tube 310. In some embodiments, the pump 331 is mounted on a side wall of the catheter tube 310 in proximity to the first opening 313 of the catheter tube 310. It is worth noting that the configuration of the pump 331 is in compatible with the embodiments of FIGS. 1A-1B, as well.

Figure 2B:
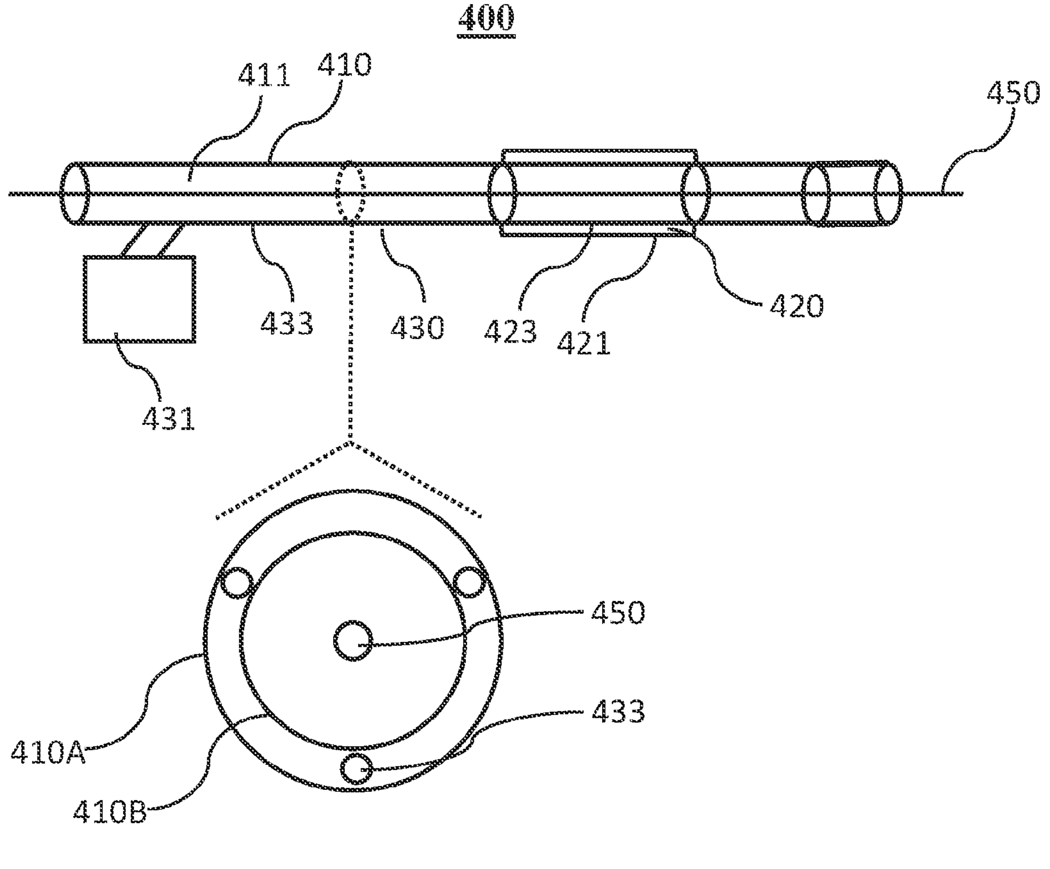

Referring to FIG. 2B, in some embodiments, the tube 433 as well as the opening 423 are inside the outer wall of the catheter tube 410. In some embodiments, the tube 433 is part of the outer wall of the catheter tube 410. In some embodiments, the tube 433 is located between an outer shaft 410A of the catheter tube 410 and an inner shaft 410B of the catheter tube 410.

Referring to FIG. 1A, in some embodiments, the guide catheter 100 further comprises a radiopaque marker 140 on the catheter tube 110, at or in proximity to the second opening 115. In some embodiments, the radiopaque marker 140 is opaque to X-ray. In some embodiments, the length of the radiopaque marker 140 along the direction of the catheter tube 110 ranges from about 2 mm to about 10 mm, such as from about 2.5 mm to about 9 mm, about 3 mm to about 8 mm, about 3.5 mm to about 7 mm, or about 4 mm to about 6 mm. In some embodiments, the length of the radiopaque marker 140 along the direction of the catheter tube 110 is about 2 mm, about 3 mm, about 4 mm, about 5 mm, about 6 mm, about 7 mm, about 8 mm, about 9 mm, about 10 mm, or any ranges therebetween.

In some embodiments, the guide catheter 100 further includes a treatment device 150 that runs inside the catheter tube 111. In some embodiments, the treatment device is a stent retriever, an aspiration catheter, or the like. In some embodiments, the treatment device 150 is not part of the catheter 100 but rather considered a separate device.

Method of Navigating Guide Catheter Near Treatment Site

In some aspects, the present invention is directed to a method of navigating a guide catheter to a predetermined site in a subject near a site in need of treatment (treatment site). In some embodiments, the treatment site is in the head or the neck of a subject. In some embodiments, the treatment site is a thrombus in a blood vessel in the head or the neck of a subject.

In some embodiments, guide catheter is the same or similar to those described elsewhere herein, such as in the "Guide Catheter" section.

In some embodiments, the method includes insert a distal end of the guide catheter into a blood vessel of the subject, and advance the guide catheter along the blood vessel until reaching the predetermined site.

In some embodiments, the guide catheter is inserted into the radial artery or the femoral artery of the subject. In some embodiments, the guide catheter is inserted into the radial artery of the subject.

In some embodiments, the predetermined site is in the carotid artery in the neck of the subject.

In some embodiments, the guide catheter is a guide catheter, and the method further includes, after navigating the guide catheter to the predetermined site, inflating the balloon to limit a blood flow.

In some embodiments, the method further includes, after navigating the guide catheter to the predetermined site, inserting a treatment device into the guide catheter, moving the treatment device along the guide catheter, and navigate the treatment device to the treatment site. In some embodiments, the treatment device is a stent-retriever, an aspiration catheter, or the like. In some embodiments, the method further includes performing treatment at the treatment site using the treatment device. In some embodiments, performing the treatment includes removing a thrombus with the treatment device.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

REFERENCE NUMBERS APPEARED IN THE FIGURES

Guide catheter: 100, 200, 300 and 400;
Catheter tube: 110, 310 and 410;

Catheter lumen: 111, 311 and 411;
First opening: 113 and 313;
Second opening: 115;
Section between the balloon and the second opening: 117;
Balloon: 120, 220, 320 and 420;
Flexible balloon material: 121, 221, 321 and 421;
Opening for inflation: 123, 223, 323 and 423;
Inflator: 130, 230, 330 and 430;
Pump: 131, 231, 331 and 431;
Tube for inflation: 133, 233, 333 and 433;
Fluid for inflation: 235;
Radiopaque marker 140;
Treatment device 150 and 450.

What is claimed is:

1. A guide catheter, comprising:

a catheter tube having
- a catheter lumen,
- a first opening, and
- a second opening;

and a balloon surrounding the catheter tube, wherein the length of the section of the catheter tube between the balloon and the second opening ranges from about 8 cm to about 25 cm;

wherein the stiffness of the catheter tube varies between the section surrounded by the balloon and the second opening; and wherein the stiffness of the catheter tube between the section surrounded by the balloon and the second opening gradually decreases toward the second opening of the catheter tube.

2. The guide catheter of claim 1, wherein the length of the catheter ranges from about 80 cm to about 110 cm.

3. The guide catheter of claim 1, wherein the outer diameter of the catheter tube ranges from about 2 mm to about 3.5 mm.

4. The guide catheter of claim 1, wherein the diameter of the catheter lumen ranges from about 1.8 mm to about 2.5 mm.

5. The guide catheter of claim 1, wherein the length of the balloon surrounding the catheter tube ranges from 5 mm to about 15 mm.

6. The guide catheter of claim 1, wherein the cross-sectional diameter of the balloon ranges from 5 mm to about 18 mm when the balloon is inflated.

7. The guide catheter of claim 1, wherein the balloon comprises a flexible balloon material comprising at least one selected from the group consisting of a nylon material, a polyester material, a polyether block amide (PEBA) material, a polyurethane material, and a silicone material.

8. The guide catheter of claim 1, wherein the section of the catheter tube between the section surrounded by the balloon and the second opening is at least partially coated by a hydrophilic coating.

9. The guide catheter of claim 8, wherein the hydrophilic coating extends from the second opening of the catheter tube for a length ranging from about 20 cm to about 25 cm.

10. The guide catheter of claim 1, further comprising an inflator for inflating the balloon.

11. The guide catheter of claim 1, further comprising a radiopaque marker on the catheter tube at or in proximity to the second opening.

12. A method of navigating the guide catheter of claim 1 to a predetermined site in a subject near a treatment site, comprising:

inserting the guide catheter into a blood vessel leading to the predetermined site;

moving the guide catheter along the blood vessel until the second opening of the catheter tube reaches the predetermined site; and after the second opening of the catheter tube reaches the predetermined site, inflating the balloon to limit blood flow in the blood vessel.

13. The method of claim 12, wherein the treatment site comprises a thrombus blocking blood flow in the subject.

14. The method of claim 12, wherein the blood vessel in which the guide catheter is inserted is a radial artery or a femoral artery.

15. The method of claim 12, wherein the predetermined site is in the carotid artery in the neck of the subject.

16. The method of claim 12, wherein the treatment site is in the head or the neck of the subject.

* * * * *